United States Patent
Zawadzki

(12)
(10) Patent No.: US 6,210,445 B1
(45) Date of Patent: Apr. 3, 2001

(54) TIBIAL KNEE COMPONENT WITH A MOBILE BEARING

(75) Inventor: Steven A. Zawadzki, Leesburg, IN (US)

(73) Assignee: Bristol-Myers Squibb Company, New York, NY (US)

(*) Notice: Subject to any disclaimer, the term of this patent is extended or adjusted under 35 U.S.C. 154(b) by 0 days.

(21) Appl. No.: 09/427,659

(22) Filed: Oct. 26, 1999

(51) Int. Cl.$^7$ .................................................. A61F 2/38
(52) U.S. Cl. .............................................. 623/20.33
(58) Field of Search .................. 623/20.14, 20.15, 623/20.21, 20.22, 20.23, 20.27, 20.28, 20.29, 20.33

(56) References Cited

U.S. PATENT DOCUMENTS

| 4,085,466 | 4/1978 | Goodfellow et al. |
| 4,094,017 | 6/1978 | Matthews et al. |

(List continued on next page.)

FOREIGN PATENT DOCUMENTS

| 0 472 475 A2 | 7/1991 | (EP). |
| 0 498 586 A1 | 1/1992 | (EP). |
| 0 519 872 A1 | 6/1992 | (EP). |
| 0 592 750 B1 | 12/1992 | (EP). |
| 0 670 151 A2 | 1/1995 | (EP). |
| 0 636 353 A1 | 2/1995 | (EP). |
| 0 674 887 A1 | 3/1995 | (EP). |
| 7920563 | 8/1979 | (FR). |
| 2 277 034 B | 10/1994 | (GB). |
| 2 278 782 A | 12/1994 | (GB). |
| 2 280 375 B | 2/1995 | (GB). |
| 2 291 355 B | 7/1995 | (GB). |
| 2 291 355 A | 1/1996 | (GB). |
| 2 293 109 A | 3/1996 | (GB). |
| 2 304 051 A | 3/1997 | (GB). |
| 2 312 166 A | 10/1997 | (GB). |
| 2 312 167 A | 10/1997 | (GB). |
| 2 312 168 A | 10/1997 | (GB). |
| 2 312 377 A | 10/1997 | (GB). |
| 2 313 314 A | 11/1997 | (GB). |
| WO 95/22303 | 8/1995 | (WO). |
| WO 95/25484 | 9/1995 | (WO). |
| WO 95/27450 | 10/1995 | (WO). |
| WO 95/30390 | 11/1995 | (WO). |
| WO 96/01087 | 1/1996 | (WO). |
| WO 96/03097 | 2/1996 | (WO). |

OTHER PUBLICATIONS

The Mechanical Testing of a Sliding Meniscus Knee Prosthesis; R.J. Minns, B.Eng., M.Sc., Ph.D., J. Campbell, CH.B., M.Ch. (Ortho), FRCS: Clinical Orthopaedies; Nov.–Dec. 1978, vol. 137; pp. 268–275.

S–ROM®Modular Total Knee System; Joint Medical Products Corp; 1993.

TRA™Knee System Design Rationale; Nov. 1996; pp. 1–23.

New Jersey LCS®Total Knee System; DePuy; 1994.

(List continued on next page.)

Primary Examiner—Todd E. Manahan
Assistant Examiner—Eduardo C. Robert
(74) Attorney, Agent, or Firm—Todd A. Dawson

(57) ABSTRACT

An orthopaedic knee component for implanting within a proximal tibia includes a tibial tray having a distally extending stem, a proximal tibial plateau and an annular shaped recess extending into the tibial plateau. The recess has a substantially constant radius of curvature about an axis of rotation. A bearing carried by the tibial tray has an articular bearing surface for engagement with a femoral component. The bearing has an annular shaped projection extending into the recess. The projection and the recess allow pivotal movement of the bearing relative to the tibial plateau about the axis of rotation.

4 Claims, 6 Drawing Sheets

U.S. PATENT DOCUMENTS

| | | |
|---|---|---|
| 4,136,405 | 1/1979 | Pastrick et al. . |
| 4,216,549 | 8/1980 | Hillberry et al. . |
| 4,219,893 | 9/1980 | Noiles . |
| 4,224,696 | 9/1980 | Murray et al. . |
| 4,224,697 | 9/1980 | Murray et al. . |
| 4,257,129 | 3/1981 | Volz . |
| 4,262,368 | 4/1981 | Lacey . |
| 4,301,553 | 11/1981 | Noiles . |
| 4,309,778 | 1/1982 | Buechel et al. . |
| 4,470,158 | 9/1984 | Pappas et al. . |
| 4,586,933 | 5/1986 | Shoji et al. . |
| 4,634,444 | 1/1987 | Noiles . |
| 4,728,332 | 3/1988 | Albrektsson . |
| 4,888,021 | 12/1989 | Forte et al. . |
| 4,950,297 | 8/1990 | Elloy et al. . |
| 5,011,496 | 4/1991 | Forte et al. . |
| 5,062,852 * | 11/1991 | Dorr et al. ................. 623/20.33 |
| 5,071,438 * | 12/1991 | Jones et al. ................. 623/20.29 |
| 5,080,675 | 1/1992 | Lawes et al. . |
| 5,171,283 | 12/1992 | Pappas et al. . |
| 5,271,747 | 12/1993 | Wagner et al. . |
| 5,282,868 | 2/1994 | Bahler . |
| 5,314,481 | 5/1994 | Bianco . |
| 5,314,483 | 5/1994 | Wehrli et al. . |
| 5,330,533 | 7/1994 | Walker . |
| 5,344,460 | 9/1994 | Turanyi et al. . |
| 5,358,527 | 10/1994 | Forte . |
| 5,358,530 | 10/1994 | Hodorek . |
| 5,358,531 | 10/1994 | Goodfellow et al. . |
| 5,370,701 | 12/1994 | Finn . |
| 5,387,240 | 2/1995 | Pottenger et al. . |
| 5,395,401 | 3/1995 | Bahler . |
| 5,413,604 | 5/1995 | Hodge . |
| 5,413,608 | 5/1995 | Keller . |
| 5,458,644 | 10/1995 | Grundei . |
| 5,480,446 | 1/1996 | Goodfellow et al. . |
| 5,549,689 * | 8/1996 | Epstein et al. ................. 623/20.23 |
| 5,556,432 | 9/1996 | Kubein-Messenburg et al. . |
| 5,609,639 | 3/1997 | Walker . |
| 5,609,644 | 3/1997 | Ashby et al. . |
| 5,658,342 | 8/1997 | Draganich et al. . |
| 5,683,468 | 11/1997 | Pappas . |
| 5,702,466 | 12/1997 | Pappas et al. . |
| 5,725,584 | 3/1998 | Walker et al. . |
| 5,879,394 | 3/1999 | Ashby et al. . |
| 6,013,103 * | 1/2000 | Kaufman et al. ................. 623/20.15 |

OTHER PUBLICATIONS

SAL Self–Aligning Total Knee Replacement; Protek.

Difficulties With Bearing Dislocation and Breakage Using a Movable Bearing Total Knee Replacement System; James K. Weaver, M.D., Robert S. Kerkash, M.D., A. Seth Greenwald D. Phil. (Oxon); Clinical Orthopaedics and Related Research: No. 290: pp. 244–252; 1993 J. B. Lippincott Company.

The Sliding Meniscus Knee Prosthesis: Design Concepts; R. J. Minns, J. Campbell.

The Design and BioMechanics of a Sliding Meniscus Knee Prosthesis; R. J. Minns; pp. 306–309.

The Oxford Meniscal Knee Phase II; Biomet Ltd.; British JBJS, May 1988.

New Jersey Tricompartmental Total Knee System with Porocoat Surgical Procedure; Frederick F. Buechel, M.D.; DePuy.

New Jersey LCS™Total Knee System with Porocoat; DePuy; JBJS vol. 67–A, No. 8; Oct. 1985.

AGC Total Knee System; Biomet Ltd., British JBJS; Nov. 1985.

Minns Meniscal Knee—A Total Prosthesis for Early Joint Degeneration; Zimmer (Swindon).

Gliding Meniscal Knee—A Major Development in Cruciate–Retaining Arthroplasty; Zimmer (Swindon).

Longer Implant Life in Three Easy Lessons; JBJS—Jul. 1998; DePuy.

SAL. Self–Aligning An Evolution in Motion; Protek; JBJS Oct. 1997.

In 1977, The LCS™Changed the Way Knee Work; Brit JBJS, Mar. 1997; DePuy.

Study the Facts—The Oxford™Knee; British JBJS Mar. 1998; Biomet Ltd.

Longer Implant Life in Three Easy Lessons; JBJS–Jul. 1998; DePuy.

* cited by examiner

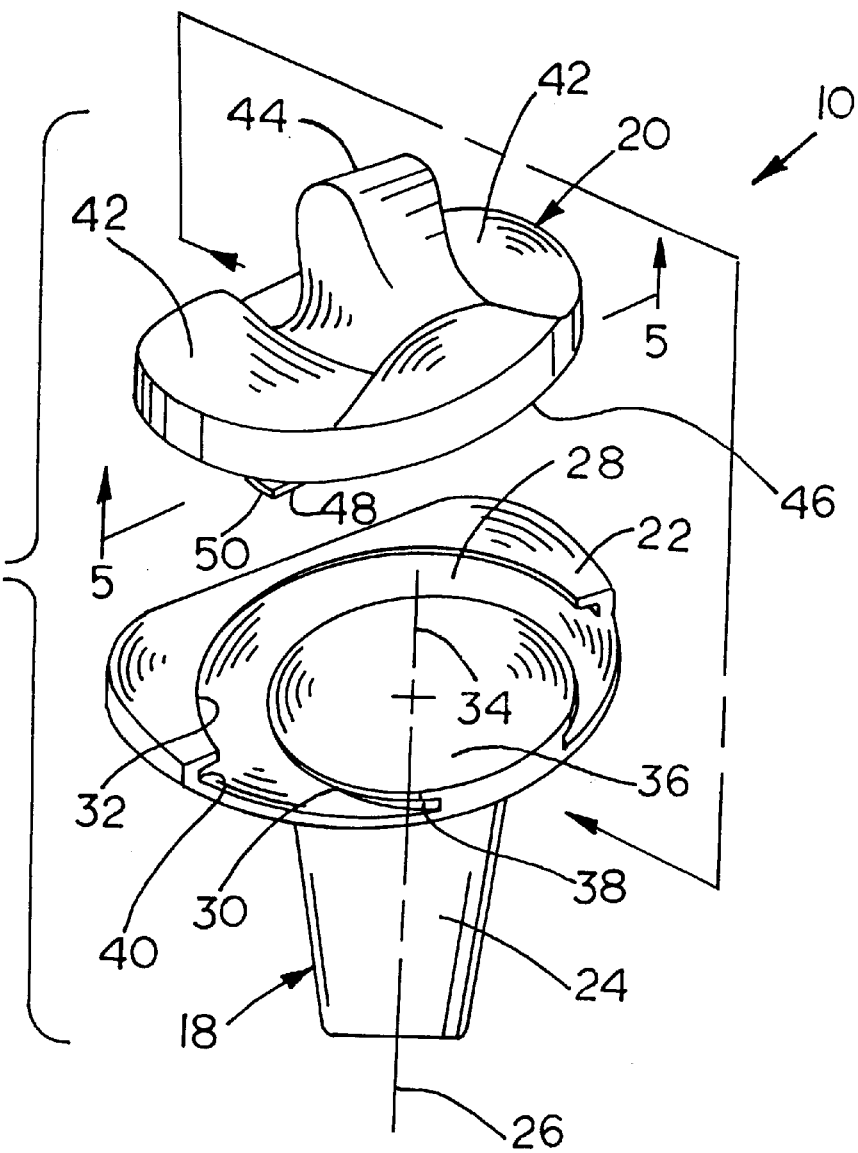

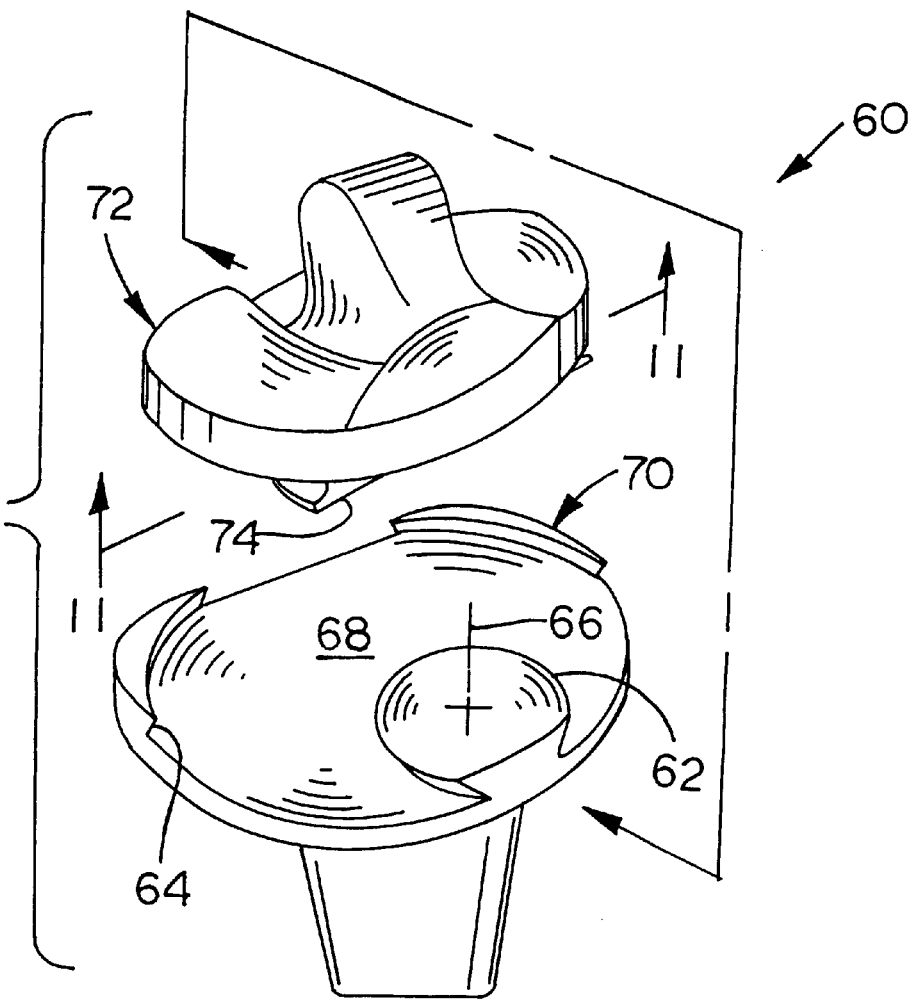
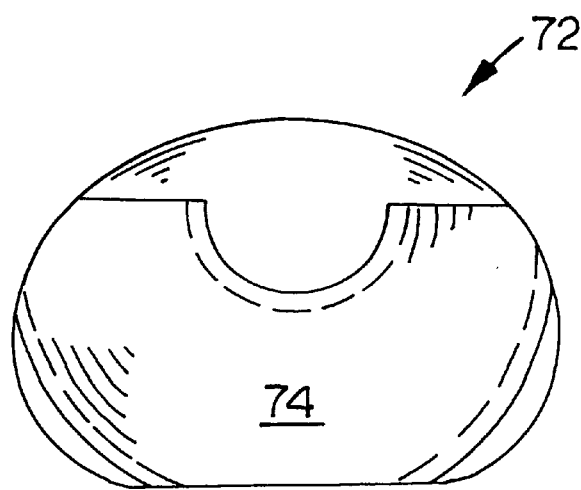

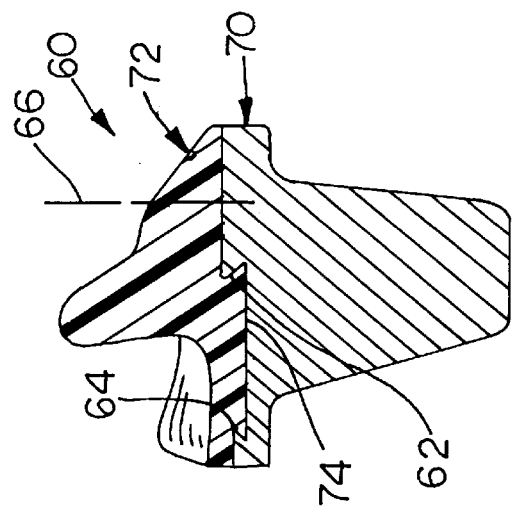
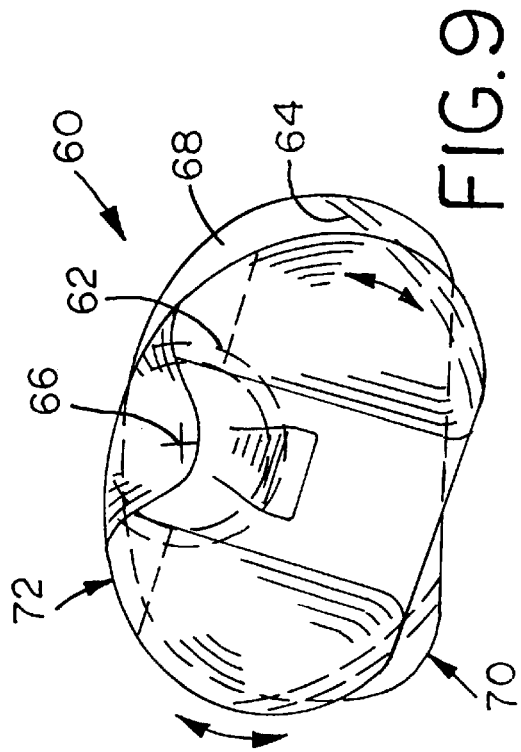
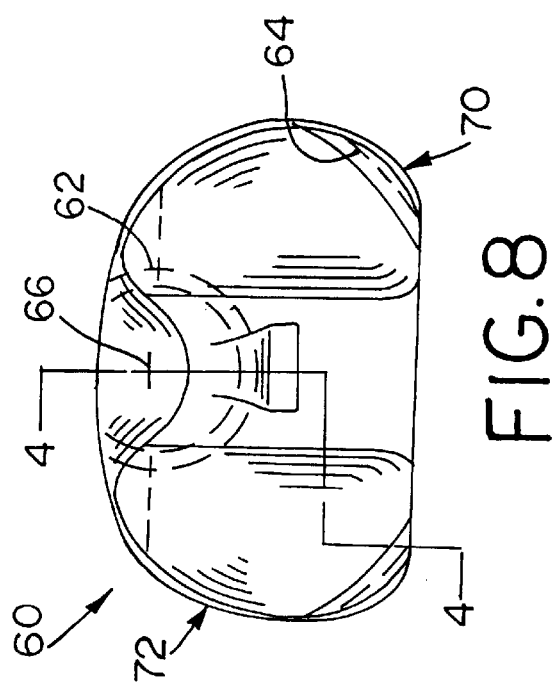

TIBIAL KNEE COMPONENT WITH A MOBILE BEARING

BACKGROUND OF THE INVENTION

1. Field of the Invention

The present invention relates to an orthopaedic implant, and, more particularly, to a tibial knee component.

2. Description of the Related Art

A tibial knee component is implanted within a proximal tibia and engages with a femoral component implanted within a distal femur. The tibial knee component typically includes a bearing which is immovably affixed to a tibial tray. The tibial tray includes a stem which is implanted within the intramedullary (IM) canal in the proximal tibia. The bearing may be in the form of a wear resistant and low friction material such as ultra high molecular weight polyethylene (UHMWPE) which is immovably attached to the tibial tray. Pivotal movement between the femoral component and the bearing surface of the bearing occurs with relatively low friction and low wear characteristics.

It is also known to provide a mobile bearing which moves relative to the tibial tray. During deep flexion between the femur and tibia, the bearing rotates about a longitudinal axis associated with a pivot point at the attachment location between the bearing and tibial tray. While some designs allow for 360 degrees of rotation between the mobile bearing and the tibial tray, most designs have a rotational limit provided. Although known designs are adequate to allow limited rotation between the bearing and tibial tray, they may be relatively complex and thus expensive to manufacture.

What is needed in the art is a tibial knee component with a mobile bearing which is easier to manufacture and still allows adequate movement between the bearing and tibial tray during deep flexion of the knee joint.

SUMMARY OF THE INVENTION

The present invention provides a tibial knee component with a tibial tray having an annular recess and a bearing having an annular projection disposed within the recess. The projection and recess allow pivotal movement of the bearing relative to the tibial tray.

The invention comprises, in one form thereof, an orthopaedic knee component for implanting within a proximal tibia. A tibial tray includes a distally extending stem, a proximal tibial plateau and an annular shaped recess extending into the tibial plateau. The recess has a substantially constant radius of curvature about an axis of rotation. A bearing carried by the tibial tray has an articular bearing surface for engagement with a femoral component. The bearing has an annular shaped projection extending into the recess. The projection and the recess allow pivotal movement of the bearing relative to the tibial plateau about the axis of rotation.

An advantage of the present invention is that the bearing is free to pivot relative to the tibial tray about an axis of rotation.

Another advantage is that the bearing is inhibited from moving in an axial direction relative to the axis of rotation.

Yet another advantage is that the annular recess and annular projection can be provided with a selected radius of curvature.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is an exploded, perspective view of an embodiment of an orthopaedic knee component of the present invention;

FIG. 5 is a bottom view of the bearing of FIGS. 1–4 as viewed along line 5—5;

FIG. 7 is an exploded, perspective view of another embodiment of an orthopaedic knee component of the present invention;

FIG. 8 is a top view of the orthopaedic knee component of FIG. 7, with the bearing in a neutral position;

FIG. 9 is a top view of the orthopaedic knee component of FIG. 7, with the bearing in a rotated position;

FIG. 10 is a side, partially sectioned view of the orthopaedic knee component of FIGS. 7–9;

FIG. 11 is a bottom view of the bearing of FIGS. 7–10 as viewed along line 11—11.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 6:
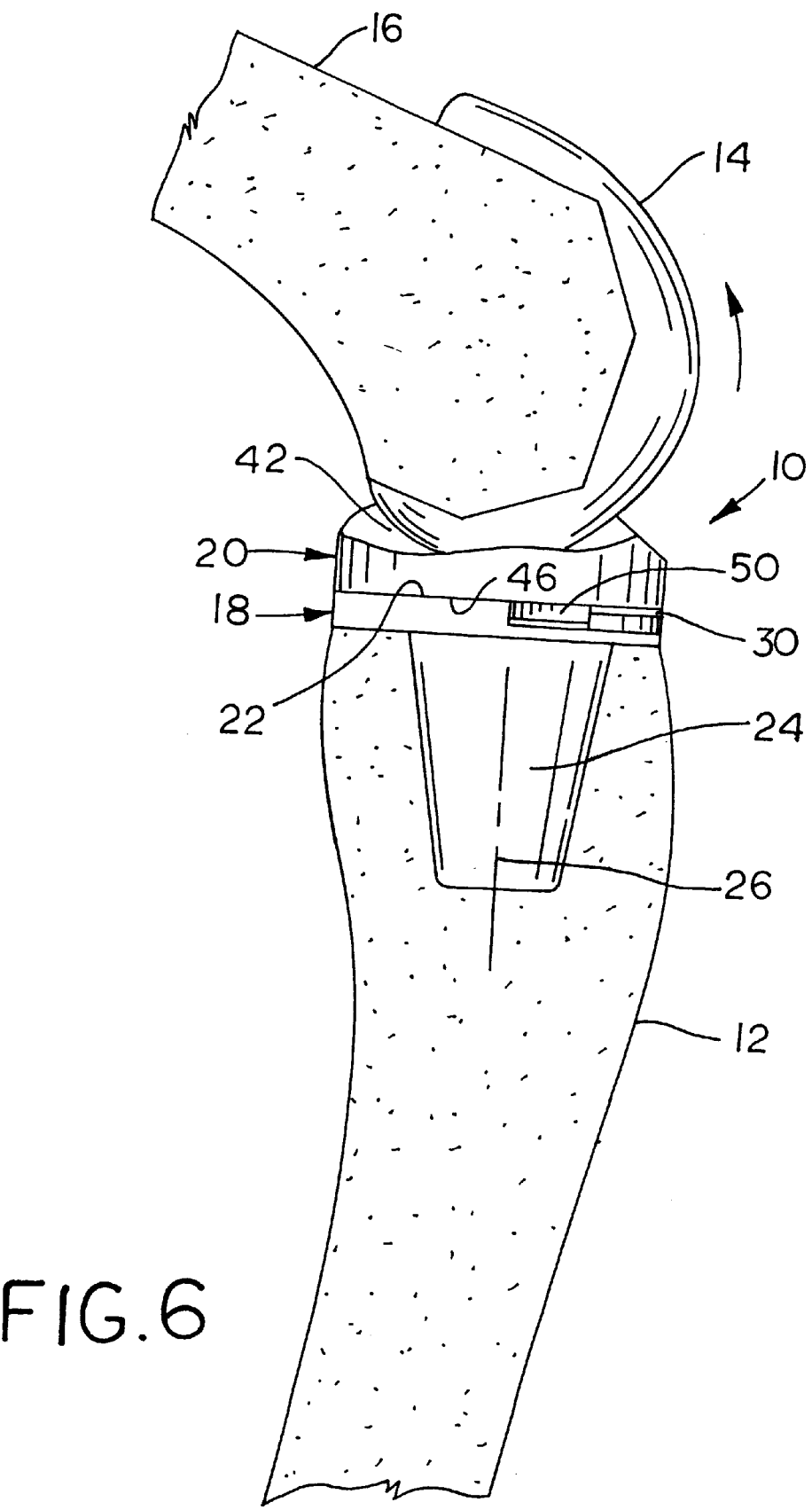
FIG. 6 is a side view of the orthopaedic knee component of FIGS. 1–4, implanted within a tibia and engaged with a femoral component.
Figure 12:
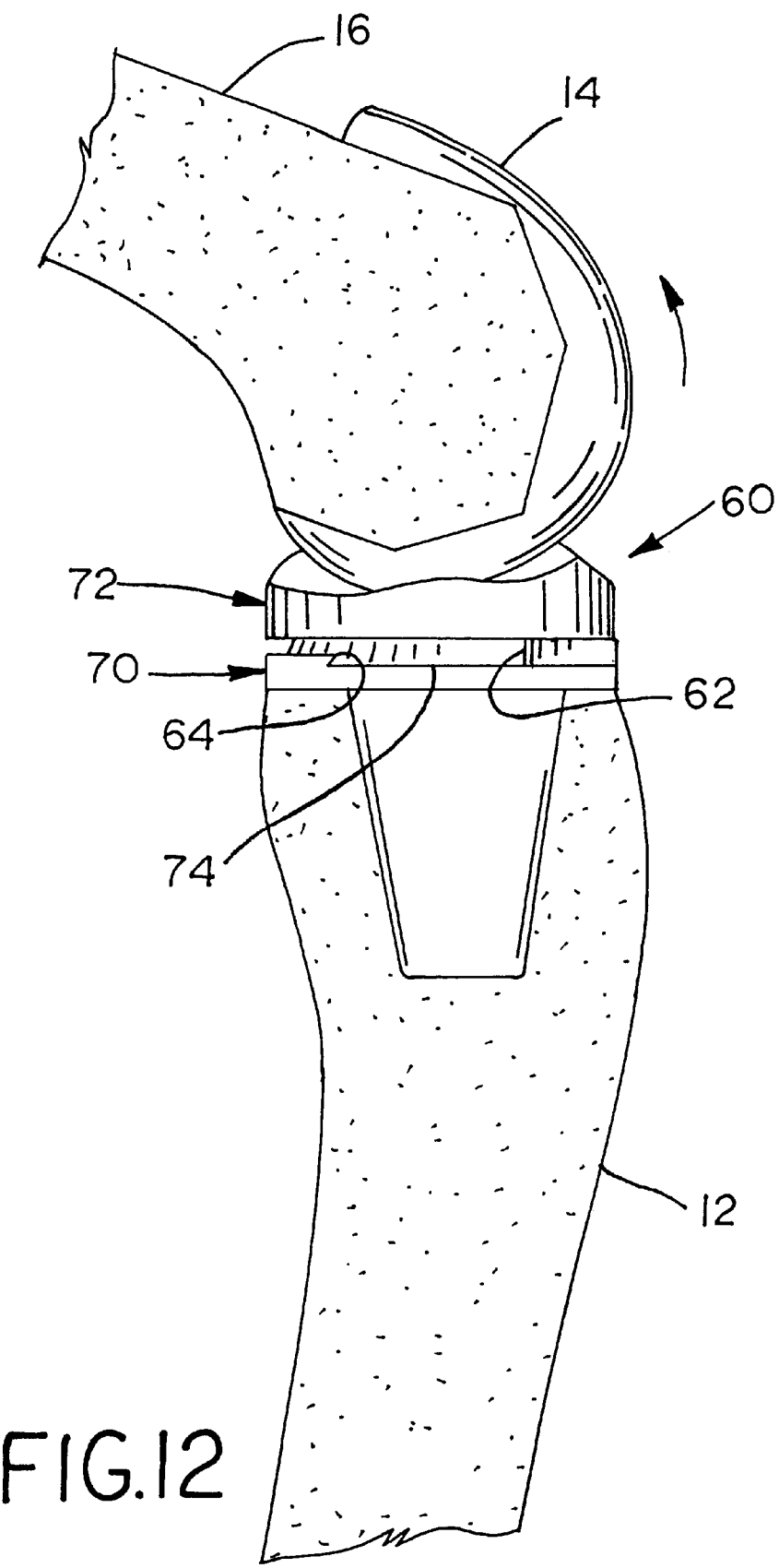
FIG. 12 is a side view of the orthopaedic knee component of FIGS. 7–10, implanted within a tibia and engaged with a femoral component.

Referring now to the drawings, and more particularly to FIGS. 1–6, there is shown an embodiment of an orthopaedic knee component in the form of a tibial knee component 10 which is implanted within a proximal tibia 12 (FIG. 6). Tibial knee component 10 engages with a femoral knee component 14 which is implanted within a distal femur 16.

Tibial knee component 10 includes a tibial tray 18 and a bearing 20. Tibial tray 18 has a proximal tibial plateau 22 and a distally extending stem 24. Tibial plateau 22 has a generally planar proximal surface which extends transverse (e.g., generally orthogonal) to a longitudinal axis 26 of stem 24.

Tibial tray 18 also includes an annular shaped recess 28 extending into tibial plateau 22. More particularly, a first annular wall 30 and a second annular wall 32 each have a substantially constant radius of curvature about an axis of rotation 34. First annular wall 30 and second annular wall 32 define recess 28 therebetween. First annular wall 30 also defines the peripheral wall of a post 36 about which bearing 20 pivots, as will be described in more detail hereinafter. First annular wall 30 and second annular wall 32 each include an undercut 38, 40, respectively. Undercut 38 of first annular wall 30 extends radially toward axis of rotation 34, and undercut 40 of second annular wall 32 extends radially away from axis of rotation 34.

Bearing 20 has an articular bearing surface 42 for engagement with femoral component 14. Articular bearing surface 42 is disposed on either side of a center projection 44. Each discrete portion of articular bearing surface 42 on either side of projection 44 engages a corresponding condyle of femoral knee component 14, with center projection 44 being disposed between the condyles.

Figure 4:
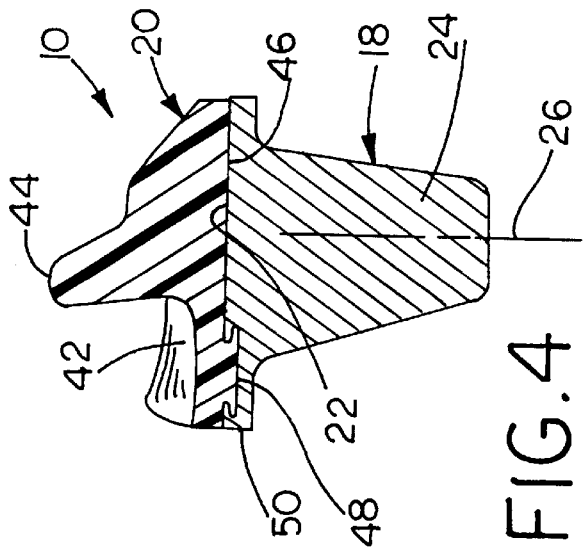
FIG. 4 is a side, partially sectioned view of the orthopaedic knee component of FIGS. 1–3.
Figure 3:
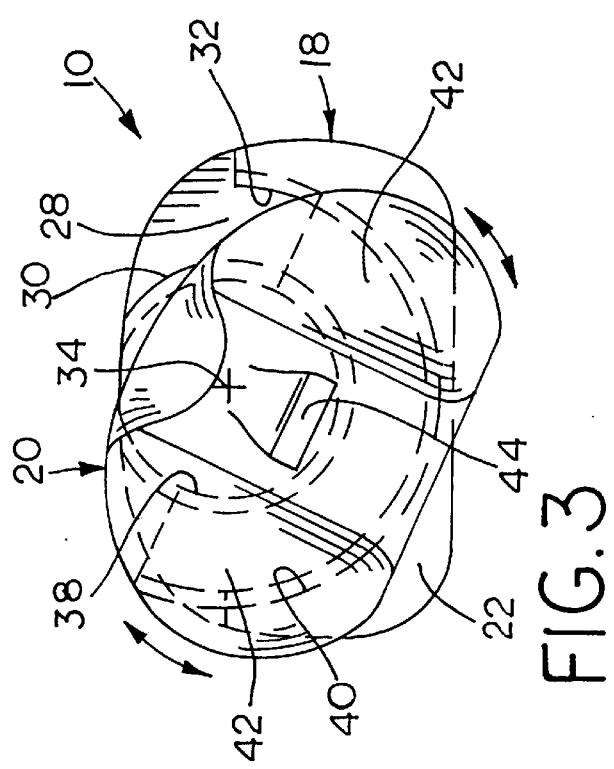
FIG. 3 is a top view of the orthopaedic knee component of FIG. 1, with the bearing in a rotated position.
Figure 2:
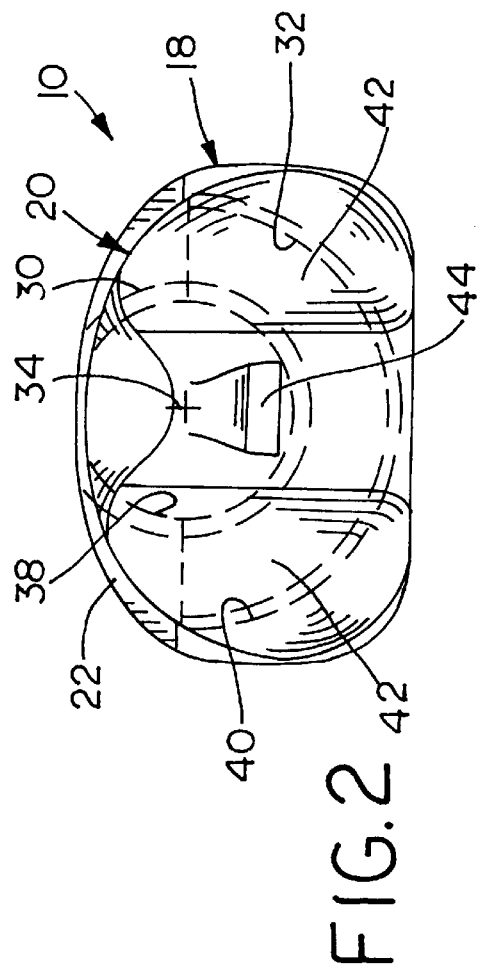
FIG. 2 is a top view of the orthopaedic knee component of FIG. 1, with the bearing in a neutral position.

Bearing 20 has a backing 46 which engages with tibial plateau 22. Backing 46 is generally planar to match the corresponding generally planar configuration of tibial plateau 22. Backing 46 defines a load bearing surface with tibial plateau 22 which transfers the load imparted either by tibial plateau 22 or the femoral condyles engaging articular bearing surface 42. Backing 46 is sized and configured such that backing 46 is substantially entirely supported by tibial plateau 22 at any position during pivotal movement between bearing 20 and tibial plateau 22. As illustrated in FIG. 2, backing 46 of bearing 20 is entirely supported by tibial plateau 22 when bearing is at a neutral position. Similarly, backing 46 is substantially entirely supported by tibial plateau 22 when bearing 20 is at a rotated position (FIG. 3), or at a position therebetween.

With a conventional tibial knee component, the tibial tray includes a notch on the posterior side such that the tibial plateau is a generally U-shape when viewed in a proximal-distal direction. Moreover, the bearing may overhang the tibial tray by a substantial amount when the bearing is at a rotational limit. On the other hand, tibial plateau 22 of the present invention does not include a notch on the posterior side and the bearing does not overhang the tibial plateau by any appreciable amount when at a neutral or rotated position. Thus, bearing 20 is better supported and wear between backing 46 and tibial plateau 22 is reduced.

Bearing 20 also includes an annular shaped projection 48 which extends from backing 46 and is received within annular shaped recess 28. Annular shaped projection 48 and annular shaped recess 28 allow pivotal movement of bearing 20 relative to tibial plateau 22 about axis of rotation 34. To inhibit relative movement between bearing 20 and tibial plateau 22 in a direction generally parallel to axis of rotation 34, projection 48 includes a pair of radially extending flanges 50 which extend into each undercut 38, 40 of first annular wall 30 and second annular wall 32. Of course, other types of keying arrangements between bearing 20 and tibial plateau 22 are also possible which allow pivotal movement therebetween while inhibiting axial movement therebetween.

The width of annular shaped recess 28 between first annular wall 30 and second annular wall 32, as well as the width of annular shaped projection 48 corresponding thereto, is selected such that annular shaped projection 48 has sufficient rigidity to allow pivotal movement between bearing 20 and tibial plateau 22. The width as well as the depth of annular shaped projection 48 may be selected empirically or theoretically, and is dependent upon the material from which bearing 20 is constructed. In the embodiment shown, bearing 20 is constructed from a plastic (e.g., UHMWPE) and tibial tray 18 is constructed from a metal (e.g., cobalt-chromium alloy).

To assemble tibial knee component 10, bearing 20 is placed adjacent tibial plateau 22 such that an end of annular shaped projection 48 extends into annular shaped recess 28 with flanges 50 respectively disposed within undercuts 38, 40. Bearing 20 is then rotated about axis of rotation 34 to a selected position, such as the neutral position shown in FIG. 2 or the rotated position shown in FIG. 3. Tibial knee component 10 may be implanted within a proximal tibia in an assembled state. Alternatively, tibial tray 18 may be implanted within a proximal tibia, after which bearing 20 is coupled with tibial tray 18 in a manner as described above.

FIGS. 7–12 illustrate another embodiment of a tibial knee component 60 of the present invention which is similar in many respects to tibial knee component 10 shown in FIGS. 1–6. The primary difference between tibial knee component 60 and tibial knee component 10 is the distance relationships between first annular wall 62 and second annular wall 64 relative to axis of rotation 66. First annular wall 62 is closer to axis of rotation 66 and second annular wall 64 is further away from axis of rotation 66, thus making the width of annular shaped recess 68 therebetween of tibial tray 70 greater than the width of annular shaped recess 28 of tibial tray 18. Accordingly, bearing 72 has an annular shaped projection 74 with a width corresponding to annular shaped recess 68 which is wider than the width of annular shaped projection 48 of bearing 20.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic knee component for implanting within a proximal tibia, comprising:

a tibial tray including a distally extending stem, a proximal tibial plateau, a post extending generally orthogonal to said tibial plateau and defining an axis of rotation, and an annular shaped recess surrounding said post and extending into said tibial plateau, said recess having a substantially constant radius of curvature about said axis of rotation; and a bearing carried by said tibial tray and having an articular bearing surface for engagement with a femoral component, said bearing having an annular shaped projection extending into said recess, said projection and said recess allowing pivotal movement of said bearing relative to said tibial plateau about said axis of rotation.

2. The orthopaedic knee component of claim 1, wherein said tibial tray includes a first annular wall and a second annular wall defining said recess, said post including said first annular wall, each of said first annular wall and said second annular wall positioned generally concentric about said axis of rotation, at least one of said first annular wall and said second annular wall including an undercut, said projection including a radially extending flange extending into said undercut.

3. The orthopaedic knee component of claim 2, wherein each said flange and said corresponding undercut define a means for inhibiting movement of said bearing relative to said tibial plateau in a direction generally axial to said axis of rotation.

4. The orthopaedic knee component of claim 2, where each of said first annular wall and said second annular wall include an undercut, and said projection includes two radially extending flanges which respectively extend into a corresponding said undercut.

* * * * *